United States Patent [19]

Kårdén et al.

[11] 4,106,750
[45] Aug. 15, 1978

[54] SAFETY VALVE FOR PNEUMATIC TOOLS

[75] Inventors: Karl Gösta Kårdén; Karl Gustav Berger, both of Nacka, Sweden

[73] Assignee: Atlas Copco Aktiebolag, Nacka, Sweden

[21] Appl. No.: 738,279

[22] Filed: Nov. 2, 1976

[30] Foreign Application Priority Data

Nov. 6, 1975 [SE] Sweden ................... 7512433

[51] Int. Cl.² .......................................... F16K 39/00
[52] U.S. Cl. .................... 251/282; 251/325; 173/169; 137/614.16
[58] Field of Search ................ 173/169; 251/66, 67, 251/282, 98, 99, 111, 325; 137/614.16

[56] References Cited

U.S. PATENT DOCUMENTS

| | | | |
|---|---|---|---|
| 1,279,087 | 9/1918 | Desmond | 251/325 |
| 1,607,343 | 11/1926 | Davenport | 251/66 |
| 1,632,144 | 6/1927 | Němec | 251/66 |
| 2,023,276 | 12/1935 | Lovekin et al. | 251/66 |
| 2,446,011 | 7/1948 | Johnson et al. | 173/169 |
| 2,778,599 | 1/1957 | Paul, Jr. | 251/66 |
| 2,939,675 | 6/1960 | Karden | 173/169 |
| 3,294,362 | 12/1966 | Schultz | 251/282 |

FOREIGN PATENT DOCUMENTS

| | | | |
|---|---|---|---|
| 28,243 | 8/1921 | Denmark | 173/169 |
| 439,128 | 1/1912 | France | 173/169 |

Primary Examiner—William R. Cline
Assistant Examiner—H. Jay Spiegel
Attorney, Agent, or Firm—Flynn & Frishauf

[57] ABSTRACT

A safety valve for pneumatic tools, comprising first and second valve bodies which are movable relative to each other and which carry cooperating seat surfaces. The first valve body is of tubular shape and is displaceable between a closed and an opened position by means of a lever.

The second valve body is pressure balanced and biased by a spring to maintain sealing contact with the first valve body as the latter is displaced. A lever operated arresting means is arranged to lock the second valve body against movement and thereby interrupt the sealing contact between the first and second valve bodies as the first valve body is displaced.

18 Claims, 3 Drawing Figures

SAFETY VALVE FOR PNEUMATIC TOOLS

BACKGROUND OF THE INVENTION

This invention relates to a safety valve for pneumatic tools. In particular the invention relates to a novel pressure air supply valve for hand held pneumatic tools.

A serious problem concerned with hand held pneumatic tools such as grinding machines and boring machines is that they very easily may get started unintentionally and thereby cause damage to people and equipment. The reason is that the power supply valve of a conventional type machine of this kind is operated by means of a lever that projects from the outside of the machine housing. The control lever thereby is exposed in a manner that increases the risk for unintentional activation.

During shorter or longer interruptions in work a machine of this type is mostly still connected to the pressure air source, and if the maneuver handle is accidentally pressed by someone or something the machine starts up uncontrolled.

SUMMARY OF THE INVENTION

This invention intends to solve the above safety problem.

In accordance with the present invention, a safety valve for pneumatic tools comprises a first valve body which is manually shiftable between a closed position and an open position, a second valve body which is movable relative to and sealingly cooperating with the first valve body, and a spring which loads the second valve body in the opening direction of the first valve body in order to maintain the sealing cooperation as the first valve body is shifted toward its opened position. Further provided is a manually operable arresting means arranged to selectively lock the second valve body against movement and to thereby discontinue the sealing cooperation between the first and second valve bodies as the first valve body is shifted toward its opened position.

DETAILED DESCRIPTION

Figure 1:
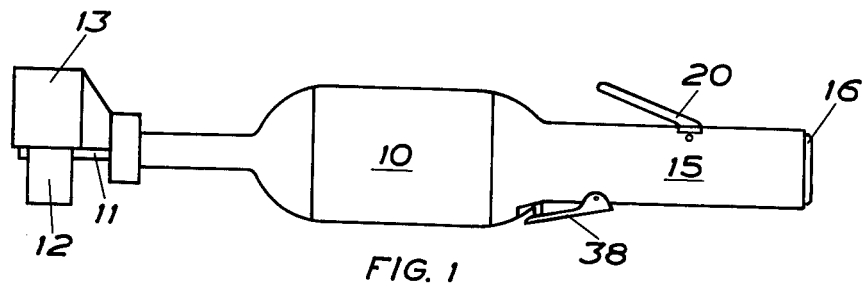
FIG. 1 shows a rotating grinding machine provided with a novel power supply valve according to the invention.

In the drawing 10 designates the housing of a grinding machine. The housing 10 lodges a pneumatic motor (not shown) which rotates an output shaft 11 and a grinding wheel 12 secured thereto. At its forward end the housing 10 is provided with a protection hood 13 which partly surrounds the grinding wheel 12.

At its rear end the housing 10 is formed with a handle 15 through which extends a pressure air inlet passage.

A nipple 16 is threaded into the rear extremity of the handle 15 to receive a matching nipple on a pressure air supply hose (not shown).

Figure 2:
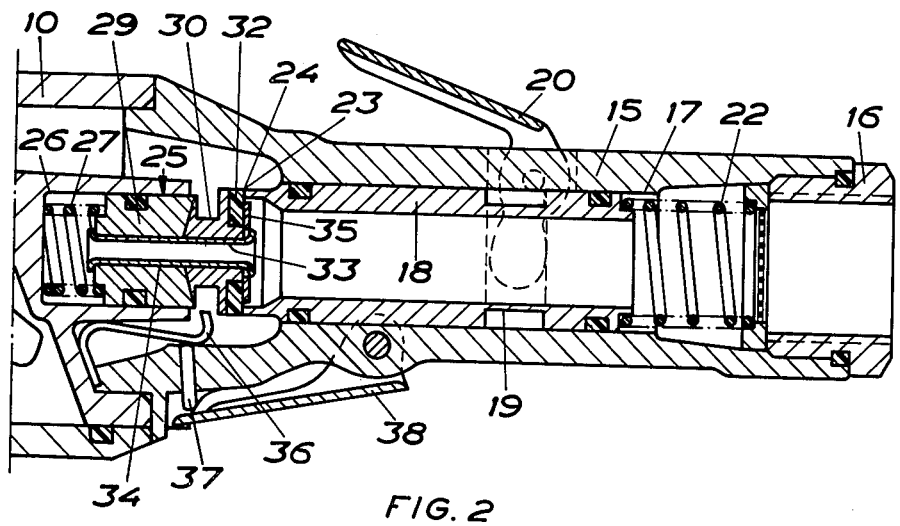
FIG. 2 shows, in larger scale, a longitudinal section through the supply valve of the machine shown in FIG. 1. The supply valve is shown in closed position.
Figure 3:
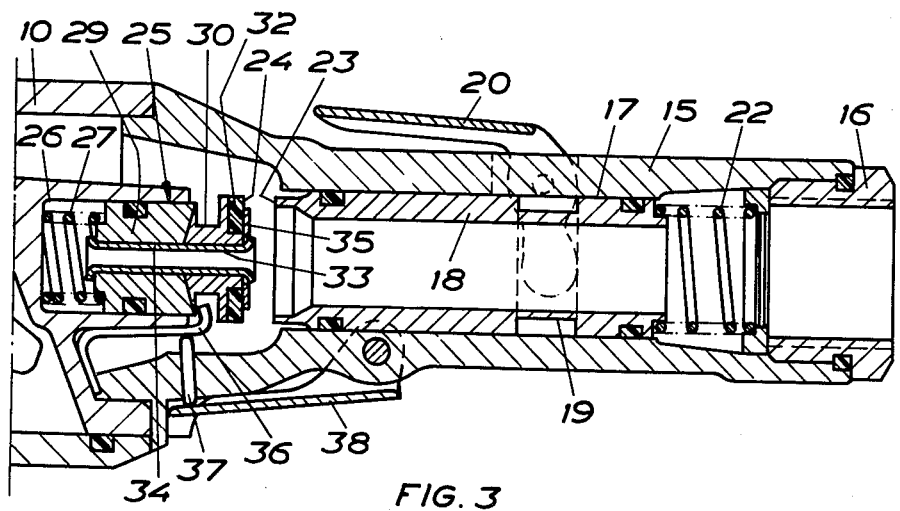
FIG. 3 shows the same section as FIG. 2 but with the valve in the opened position.

Referring to FIGS. 2 and 3 within the handle 15 the pressure air supply passage is partly formed by a cylindrical bore 17 in which there is sealingly guided a first valve body 18. The latter is constituted by a tube shaped sleeve having on its outer periphery an annular groove 19. A maneuver lever 20 pivotably supported on the handle 15 has a forked rear end which engages the annular groove 19 for longitudinal displacement of the valve body 18 between a closed position, shown in FIG. 2, and an opened position shown in FIG. 3.

A coil spring 22 which is supported between the rear end of valve body 18 and nipple 16 biases the valve body 18 towards its closed position.

At its forward end the first valve body 18 is provided with an annular seat surface 23 which is arranged to sealingly cooperate with a matching seat surface 24 on a second valve body 25.

The second valve body 25 is displaceable relative to valve body 18 and is sealingly guided in a bore 26 which is coaxial with bore 17. Valve body 25 is biased towards valve body 18 by a spring 27 and comprises a cylindrical portion 29 formed with an annular groove 30. At its rear end valve body 25 is provided with a resilient ring 32 which is formed with the seat surface 24. For pressure balancing purposes, valve body 25 is provided with an axially extending passage 33. The passage 33 is formed by a tube 34 which is axially fixed relative to valve body 25 by upsetting at both ends. At its rear end the tube 34 is used as a retainer for the resilient ring 32. The axial clamping force of the upset ended tube 34 is distributed over a substantial part of the resilient ring 32 by means of a washer 35.

The supply valve also comprises an arresting means 36 which in the shown embodiment of the invention is constituted by a Z-shaped leaf spring which at its one end is clamped between the handle 15 and the housing 10. The arresting means 36 is activated by a pin 37 and a lever 38 which is pivotably supported on the handle 15. By pressing the lever 38 the arresting means 36 is brought into engagement with the annular groove 30 of the second valve body 25 (see FIG. 3).

The valve according to the disclosed embodiment has the following functional features.

As the tool via nipple 16 is connected to a pressure air source and levers 20 and 38 occupy their rest positions the first and second valve bodies, 18 and 25 respectively, are pressed together by springs 22 and 27, and a sealing contact is maintained between the seat surfaces 23 and 24. The power supply to the machine is shut off (see FIG. 2).

By means of the pressure equalizing passage 33, pressure air can reach the forward end as well of the valve body 25 thereby preventing the latter from being displaced by the air pressure.

If the lever 20 now should be unintentionally pressed down, the valve body 18 would be displaced toward its opened position, e.g. to the right in FIG. 2. However, the second valve body 25 would still maintain its sealing contact with valve body 18 by action of spring 27, and the power supply to the tool would still be shut off.

To open the valve and to start up the tool the levers 20 and 38 have to be pressed down simultaneously, whereby on one hand second valve body 25 is locked against axial movement by engagement of arresting means 36 in the groove 30, and on the other hand first valve body 18 is shifted from its closed to its opened position. The seat surfaces 23, 24 of the valve bodies 18, 25 are separated and pressure air may pass the valve (see FIG. 3).

Thus, a condition for starting up and running the tool is to press down the two independent levers 20, 38 at the same time. This means that accidental starting of the tool is effectively avoided.

The safety valve according to the present invention is not limited to the shown and described embodiment but can be freely varied within the scope of the invention as it is defined by the claims.

We claim:

1. A safety valve for pneumatic tools, comprising:
a first movable valve member (18) manually shiftable between a closed position and an opened position;
a second movable valve member (25) movable relative to and selectively sealingly cooperating with said first valve member (18) to selectively open and close a pressure line;
a spring (27) loading said second valve member (25) in the opening direction of said first valve member (18), so as to maintain said sealing cooperation as said first valve member (18) is shifted toward its opened position; and
manually operable arresting means (36,37,38) coupled to said second valve member (25) to selectively lock said second valve member (25) against movement and thereby discontinue said sealing cooperation as said first valve member (18) is shifted toward its opened position, said second valve member (25) being freely movable with said first valve member (18) while maintaining said sealing cooperation when not engaged by said arresting means.

2. Safety valve according to claim 1, wherein said first and second valve members each comprise interacting seat means (23,24) for establishing said sealing cooperation.

3. Safety valve according to claim 2, wherein said first valve member comprises a cylindrical sleeve (18), one end surface of which forms said seat means of said first valve member.

4. Safety valve according to claim 3, wherein said first, sleeve shaped valve member (18) is sealingly guided in a cylindrical bore (17) which forms a part of the pressure air inlet passage of the pneumatic tool.

5. Safety valve according to claim 3, wherein said cylindrical sleeve (18) is located upstream of said second valve member (25), and said second valve member (25) further comprising a pressure equalizing passage (33) extending substantially axially therethrough and in communication with the interior of said cylindrical sleeve (18) for pressure balancing said second valve member (25).

6. Safety valve according to claim 5, wherein said second valve member is sealingly arranged in a bore and is movable axially of said bore, said pressure equalizing passage (33) extending substantially axially through said bore.

7. Safety valve according to claim 2, wherein said first valve member (18) is located upstream of said second valve member (25), and further comprising a pressure equalizing passage (33) past said second valve member (25) for pressure balancing said second valve member.

8. Safety valve according to claim 7, wherein said pressure equalizing passage (33) extends substantially axially through said second valve member (25).

9. Safety valve according to claim 1, wherein said arresting means comprises a generally Z-shaped leaf spring (36) which is arranged to be brought into locking engagement with said second valve member (25) by bending.

10. Safety valve according to claim 9, wherein said second valve member (25) has a recess (30) therein, one leg of said generally Z-shaped leaf spring (36) being selectively engageable in said recess.

11. Safety valve according to claim 10, wherein said leg of said generally Z-shaped leaf spring (36) is biased out of engagement with said recess (30), and comprising means (37,38) for selectively engaging said leg of said leaf spring with said recess against said bias.

12. Safety valve according to claim 9, comprising means (20) engageable with said first valve member (18) for shifting same between said closed and opened positions.

13. Safety valve according to claim 12, wherein said first valve member (18) has a recess (19) therein, said shifting means (20) engaging said recess and shifting said first valve member between said closed and opened positions.

14. Safety valve according to claim 13, wherein said shifting means and arresting means comprise respective manually operable levers.

15. Safety valve according to claim 1, wherein said first valve member (18) defines a shiftable valve seat (23), and said second valve member (25) comprises a seat surface (24) for selectively sealingly cooperating with said seat (23) of said first valve member (18).

16. Safety valve according to claim 15, wherein said first valve member comprises a cylindrical sleeve (18), the end of said sleeve defining a cylindrical valve seat (23).

17. Safety valve according to claim 16, wherein said cylindrical sleeve (18) is located upstream of said second valve member (25), and said second valve member (25) further comprising a pressure equalizing passage (33) extending substantially axially therethrough and in communication with the interior of said cylindrical sleeve (18) for pressure balancing said second valve member (25).

18. Safety valve according to claim 17, wherein said second valve member is sealingly arranged in a bore and is movable axially of said bore, said pressure equalizing passage (33) extending substantially axially through said bore.

* * * * *